United States Patent [19]

Nakagawa et al.

[11] 4,145,542

[45] Mar. 20, 1979

[54] 5-[1-HYDROXY-2-(HETEROCYCLIC-AMINO)]ALKYL-8-HYDROXY-3,4-DIHYDROCARBOSTYRIL DERIVATIVES

[75] Inventors: Kazuyuki Nakagawa, Tokushima; Shiro Yoshizaki, Naruto; Shigeharu Tamada; Kaoru Tanimura, both of Tokushima, all of Japan

[73] Assignee: Otsuka Pharmaceutical Co., Ltd., Tokyo, Japan

[21] Appl. No.: 745,894

[22] Filed: Nov. 29, 1976

Related U.S. Application Data

[63] Continuation-in-part of Ser. No. 536,516, Dec. 26, 1974, Pat. No. 3,994,901.

[30] Foreign Application Priority Data

Jun. 13, 1974 [JP] Japan .................................. 49-67824

[51] Int. Cl.$^2$ .................. C07D 413/06; C07D 401/06
[52] U.S. Cl. ..................................... 544/128; 544/363
[58] Field of Search ................ 260/247.2 A, 268 BQ; 544/128, 363

[56] References Cited

U.S. PATENT DOCUMENTS 3,994,901 11/1976 Nakagawa et al. ............ 240/288 CE

OTHER PUBLICATIONS

Nakagawa et al., "Chem. Abstracts", vol. 83 (1975) No. 193, 105h.

*Primary Examiner*—Natalie Trousof
*Assistant Examiner*—R. W. Ramsuer
*Attorney, Agent, or Firm*—Sughrue, Rothwell, Mion, Zinn and Macpeak

[57] ABSTRACT

5-[1-Hydroxy-2-(heterocyclic-amino)]alkyl-8-hydroxy-3,4-dihydrocarbostyril derivatives having the formula (I)

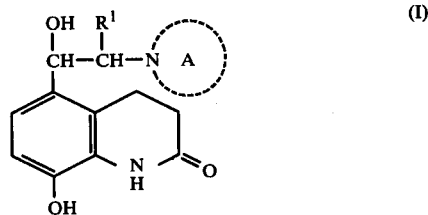

wherein $R^1$ represents an alkyl group having 1 to 4 carbon atoms and A, when taken together with the nitrogen atom to which it is attached, form a 5- or 6-membered substituted or unsubstituted heterocyclic ring containing 1 or 2 nitrogen, or oxygen atoms as hetero atoms, the pharmaceutically acceptable acid addition salts thereof, and a process for preparing the same.

3 Claims, No Drawings

5-[1-HYDROXY-2-(HETEROCYCLIC-AMINO)]ALKYL-8-HYDROXY-3,4-DIHYDROCARBOSTYRIL DERIVATIVES

RELATIONSHIP TO OTHER APPLICATIONS

This application is a continuation-in-part application of Ser. No. 536,516, filed Dec. 26, 1974, now U.S. Pat. No. 3,994,901.

BACKGROUND OF THE INVENTION

1. Field of the Invention

This invention relates to novel carbostyril derivatives and a process for preparing the same. More particularly, this invention relates to novel 5-[1-hydroxy-2-(heterocyclic-amino)]-alkyl-8-hydroxy-3,4-dihydrocarbostyril derivatives, the pharmaceutically acceptable acid addition salts thereof, and a process for preparing the same.

2. Description of the Prior Art

It is well known that certain carbostyril derivatives exhibit useful pharmaceutical activites. Representative compounds of this type have been disclosed in *Journal of Medical Chemistry*, Vol. 15, No. 3, pp. 260–266 (1972), Japanese Pat. Publication No. 38789/1971 and *Chemical Abstracts*, 62, 16212e (1965), etc. However, these prior art references do not teach that the compounds having a 1-hydroxy-2-(heterocyclic-amino)alkyl group at the 5-position of the carbostyril moiety possess an excellent β-adreno-receptor stimultating activity.

It has now been found that 8-hydroxy-3,4-dihydrocarbostyril derivatives having a 1-hydroxy-(2-heterocyclic-amino)alkyl group at the 5-position of the carbostyril moiety and the pharmaceutically acceptable acid addition salts thereof possess a β-adreno-receptor stimulating activity, and therefore, are useful as a therapeutic agent such as a bronchodilator, a peripheral vasodilator and an antihypertensive agent, particularly for treating bronchial asthma.

SUMMARY OF THE INVENTION

This invention provides novel 5-[1-hydroxy-2-(heterocyclic-amino)]alkyl-8-hydroxy-3,4-dihydrocarbostyril derivatives having the formula (I)

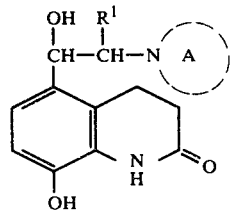

wherein $R^1$ represents an alkyl group having 1 to 4 carbon atoms and A, when taken together with the nitrogen atom to which it is attached, form a 5- or 6-membered substituted or unsubstituted heterocyclic ring containing 1 or 2 nitrogen, or oxygen atoms as hetero atoms.

This invention also provides a process for preparing the above 5-[1-hydroxy-2-(heterocyclic-amino)]alkyl-8-hydroxy-3,4-dihydrocarbostyril derivatives respresented by the formula (I)

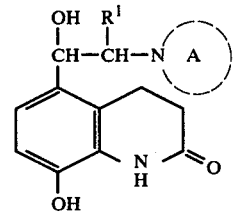

wherein $R^1$ represents an alkyl group having 1 to 4 carbon atoms and A, when taken together with the nitrogen atom to which it is attached, form a 5- or 6-membered substituted or unsubstituted heterocyclic ring containing 1 or 2 nitrogen, or oxygen atoms as hetero atoms, and the pharmaceutically acceptable acid addition salts thereof which comprises the steps of:

(1) reacting a 8-substituted-3,4-dihydrocarbostryil of the formula (VI)

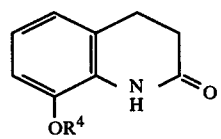

wherein $R^4$ represents a hydrogen atom or an alkyl group having 1 to 4 carbon atoms, with an α-haloalkanoic acid of the formula (V)

wherein $R^1$ is as defined above and X and X', which may be the same or different, each represents a halogen atom, in the presence or absence of a solvent and in the presence of a Lewis acid catalyst, to produce the corresponding 5-(α-haloalkanoyl)-8-substituted-3,4-dihydrocarbostyril of the formula (IV)

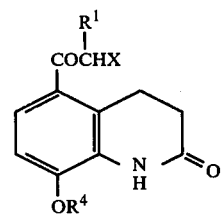

wherein $R^1$, $R^4$ and X are as defined above, (2) reacting the resulting 5-(α-haloalkanoyl)-8-substituted-3,4-dihydrocarbostyril of the formula (IV) with an amine of the formula (III)

wherein A is as defined above, to produce a 5-(α-aminoalkanoyl)-8-alkoxy-3,4-dihydrocarbostyril of the formula (IIa)

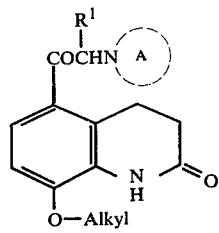

wherein "Alkyl" represents an alkyl group having 1 to 4 carbon atoms and $R^1$, A is as defined above, or a 5-(α-heterocyclic-aminoalkanoyl)-8-hydroxy-3,4-dihydrocarbostyril of the formula (IIb)

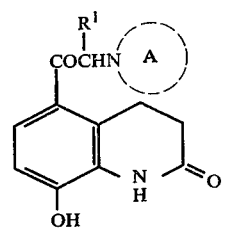

wherein $R^1$, A is as defined above, and dealkylating the carbosyril of the formula (IIa) with a hydrogen halide to produce the 5-(α-heterocyclic-aminoalkanoyl)-8-hydroxy-3,4-dihydrocarbostyril of the formula (IIb), and (3) reducing the resulting 5-(α-heterocyclic-aminoalkanoyl)-8-hydroxy-3,4-dihydrocarbostyril with hydrogen in the presence of a hydrogenation catalyst or with a reducing agent.

The 5-[1-hydroxy-2-(heterocyclic-amino)]alkyl-8-hydroxy-3,4-dihydrocarbostyril derivatives of the formula (I) and the acid addition salts thereof are novel compounds and exhibit a β-adreno-receptor stimulating activity and, therefore, are useful as a bronchodilator, a peripheral vasodilator or an antihypertensive agent, particularly for treating bronchial asthma.

DETAILED DESCRIPTION OF THE INVENTION

The term "Alkyl" as used herein means a straight or branched chain alkyl group having 1 to 4 carbon atoms, and includes, for example, a methyl, ethyl, propyl, isopropyl, butyl, sec-butyl, tert-butyl group and the like.

The term "5- or 6-membered substituted or unsubstituted heterocyclic ring" used herein means heterocyclic groups containing 1 or 2 nitrogen, or oxygen atoms as hetero atoms such as a morpholino, piperazino, or a like group which can be unsubstituted or substituted with an alkyl group having 1 to 4 carbon atoms, such as a methyl, ethyl, isopropyl, tert-butyl group and the like, for example, a N-methylpiperazino group and the like.

The compounds of the present invention represented by the formula (I) can be prepared from 8-hydroxy-3,4-dihydrocarbostyril according to the following reaction scheme:

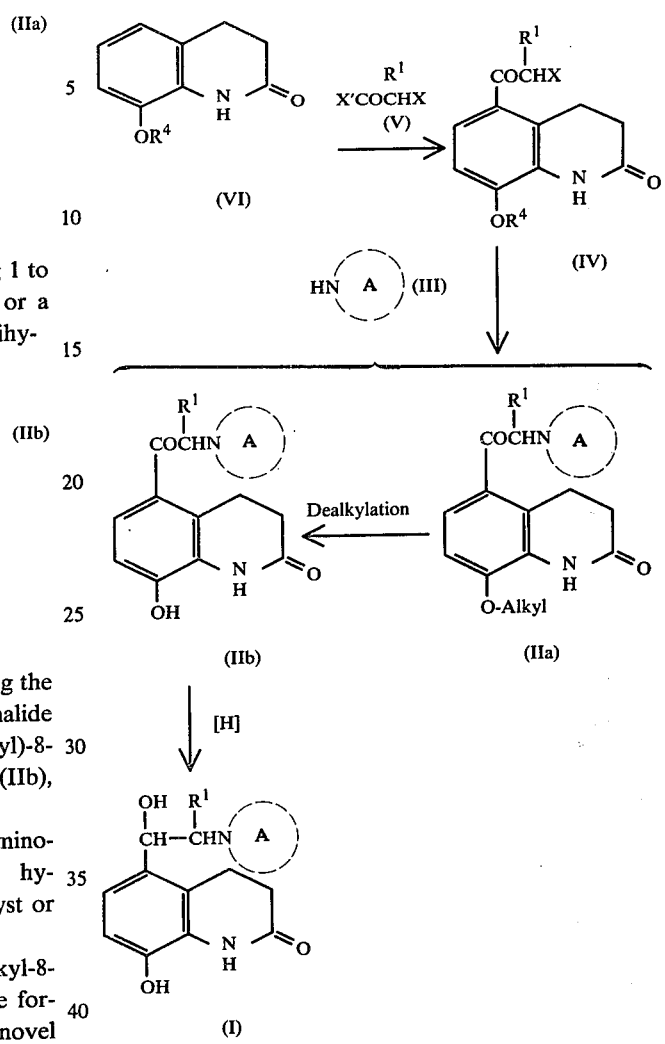

wherein $R^1$ represents an alkyl group having 1 to 4 carbon atoms; A, when taken together with the nitrogen atom to which it is attached, form a 5- or 6-membered substituted or unsubstituted heterocyclic ring containing 1 or 2 nitrogen, or oxygen atoms as hetero atoms; $R^4$ represents a hydrogebn atom or an alkyl group having 1 to 4 carbon atoms; and X and X', which may be the same or different, each represents a halogen atom.

The 8-substituted-3,4-dihydrocabostyril of the formula (VI) used as a starting material in the preparation of the compounds of the formula (IV) is a known compound and can easily be prepared by, for example, the method as disclosed in J. D. Loudon and J. Ogg; J. Chem. Soc., 1955, 739 or Fritz Mayer, L. van Zutphen and H. Philips. Ber., 60, 858 (1927).

As illustrated in the above reaction scheme, the 5-(α-haloalkanoyl)-8-substituted-3,4-dihydrocrbostyril represented by the formula (IV) which is an intermediate in the process of this invention can be prepared by reacting the corresponding 8-substituted-3,4-dihydrocarbostyril of the formula (VI) with an α-haloalkanoic acid halide of the formula (V)

wherein $R^1$, X and X' are as defined above, in the presence of a Lewis acid.

The thus obtained 5-(α-haloalkanoyl)-8-alkoxy-3,4-dihydrocarbostyril ($R^4$=alkyl) or 5-(α-haloalkanoyl)-8-hydroxy-3,4-dihydrocarbostyril ($R^4$=H) of the formula (IV) is then reacted with a secondary or tertiary organic amine represented by the formula (III)

wherein A is as defined above, in the presence or absence of a solvent to obtain a 5-(heterocyclic-aminoalkanoyl-8-substituted-3,4-dihydrocarbostyril derivative represented by the formula (II)

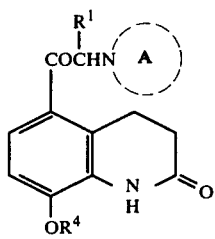

wherein $R^1$, A, and $R^4$ are as defined above, i.e., when $R^4$ is an alkyl group, the corresponding 5-(α-heterocyclic-amino-alkanoyl)-8-alkoxy-3,4-dihydrocarbostyril derivative represented by the formula (IIa)

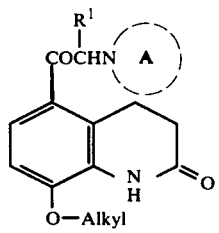

wherein "Alkyl" represents an alkyl group having 1 to 4 carbon atoms as defined for $R^4$ and $R^1$, A is as defined above, or when $R^4$ is a hydrogen atom, a 5-(heterocyclic-aminoalkanoyl)-8-hydroxy-3,4-dihydrocarbostyril represented by the formula (IIb)

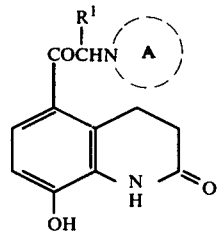

wherein $R^1$, annd A are as defined above, respectively.

The 8-alkoxy compound of the formula (IIa) as obtained above can then be dealkylated with a hydrogen halides such as hydrogen bromide to form the corresponding 8-hydroxy compound of the formula (IIb).

the 5-[1-hydroxy-2-(heterocyclic-amino)]alkyl-8-hydroxy-3,4-dihydrocarbostyril derivative of the formula (I) of the present invention can be prepared by reducing the above obtained 5-(α-heterocyclic-aminoalkanoyl)-8-hydroxy-3,4-dihydrocarbostyril derivative of the formula (IIb).

Both of the compounds (IIb) and the compounds (I) of the present invention are novel compounds.

The process according to the present invention will be hereinafter illustrated in greater detail.

The α-haloalkanoic acid halide of the formula (V) which can be used in the present invention as a reactant in the preparation of the compound of the formula (IV) includes α-chloropropionyl chloride, α-bromopropionyl chloride, α-chlorobutyryl chloride, α-bromobutyryl chloride, α-bromobutyryl bromide, α-chlorovaleryl chloride and the like, perferably, α-chloropropyl chloride and α-chlorobutyl chloride. The reaction between the 3,4-dihydrocarbostyril of the formula (VI) and the α-haloalkanoic acid halide of the formula (V) is a so-called Friedel-Crafts reaction.

The catalyst which can be used in this reaction is a usual Lewis acid, for example, aluminum chloride or bromide, zinc chloride, ferric chloride, stannic chloride, titanium chloride, boron trifluoride and the like with aluminum chloride being perferably used. These catalysts are generally used in an amount of from 2 to 10 moles, preferably 3 to 6 moles, per mole of the compound of the formula (IV).

This reaction can be effected either in the absence of a solvent or in the presence of an inert organic solvent. Suitable examples of solvents which can be used in this reaction are carbon disulfide, nitrobenzene, diethyl ether, dioxane and the like, preferably, carbon disulfide. These solvents are usually used in a volume of about 0.5 to about 20, preferably 2 to 10, times the volume of the reactants.

This reaction is generally conducted using an equimolar amount to a large excess of the α-haloalkanoic acid halide of the formula (V) of about 2 to about 20 moles, preferably 2 to 10 moles, of the α-haloalkanoic acid halide of the formula (IV) per mole of the 8-substituted-3,4-dihydrocarbostyril of the formula (VI). The reaction proceeds at room temperature (about 20° to 30° C.) to about 150° C., preferably room temperature to 80° C. The reaction time varies depending upon the reaction temperature employed, but is usually from about 1 to 20, preferably 1 to 10 hours. The reaction can preferably be carried out under anhydrous conditions.

The amine of the formula (III) which can be used as a reactant in the preparation of the 5-α-heterocyclic-aminoalkanoyl)-8-substituted-3,4-dihydrocarbostyrils of the formulae (IIa) and (IIb) includes substituted or unsubstituted heterocyclic amines, for example, morpholine, piperazine, N-methylpiperazine and the like.

The reaction between the 5-(α-haloalkanoyl)-8-substituted-3,4-dihydro-carbostyril intermediate of the formula (IV) and the amine of the formula (III) can be carried out either in the absence of a solvent because the amine of the formula (III) per se serves as a reaction solvent, or in the presence of an appropriate solvent. Suitable examples of solvents which can be used in this reaction include lower alcohols such as methanol, ethanol, isopropanol and the like, ethers such as dioxane, diethyl ether and the like, esters such as ethyl acetate, aromatic hydrocarbons such as benzene, toluene, xylene and the like, nitrile solvents such as acetonitrile and the like. Ethanol and isopropanol are preferably used.

This reaction can be effected using an equimolar amount to a large excess of the amine of the formula (III), preferably from about 2 to about 10 moles of the amine of the formula (III) per mole of the 5-(α-haloalkanoyl)-8-hydroxy-3,4-dihydrocarbostyril of the formula (IV) at room temperature to the refluxing temperature of the reaction system, preferably 40° to 100° C. at atmospheric pressure to 10 atmospheres. When the reaction is effected without using any solvent, it is preferable to use a large excess of the amine of the formula (III) with respect to the carbostyril derivative of the formula (IV).

Thus, when the 8-hydroxy-3,4-dihydrocarbostyril of the formula (VI) wherein $R^4$ is a hydrogen atom is used as a starting material, the 5-(α-heterocyclic-aminoalkanoyl)-8-hydroxy-3,4-dihydrocarbostyril of the formula (IIb) is obtained, which can be subjected to the subsequent reduction reaction to produce the 5-[1-hydroxy-2-(heterocyclic-amino)]alkyl-8-hydroxy-3,4-dihydroxycarbostyril of the formula (I). When the 8-alkoxy-3,4-dihydro-carbostyril of the formula (VI) wherein $R^4$ is an alkyl group is used as a starting material, the corresponding 5-(α-heterocyclic-aminoalkanoyl)-8-alkoxy-3,4-dihydrocarbostyril of the formula (IIa) is obtained. The resulting 5-(α-heterocyclic-aminoalkanoyl)-8-alkoxy-3,4-dihydrocarbostyril of the formula (IIa) is then reacted with a hydrogen halide to dealkylate the 8-position of the 3,4-dihydrocarbostyril moiety thereby obtaining the compound of the formula (IIa), which can be subjected to the subsequent reduction reaction as indicated above.

The hydrogen halides used in this dealkylation include, for example, hydrogen bromide, hydrogen chloride, hydrogen iodide and the like, preferably, hydrogen bromide. These hydrogen halides can advantageously be employed in an appropriate solvent such as methanol, ethanol, propanols, preferably water, in a form of an aqueous solution of the hydrogen halide at a concentration of about 10 to 50%, preferably 47% hydrogen bromide.

This dealkylation reaction can generally be carried out using the hydrogen halide in an equimolar amount to, preferably, a large excess with respect to the compound of the formula (IIa) by heating at a temperature of from about 100° to about 150° C., preferably at reflux, for about 1 to about 20 hours, preferably 3 to 10 hours.

The reduction of the above obtained 5-substituted-aminoalkanoyl8-hydroxy-3,4-dihydrocarbostyril derivative of the formula (IIb) to the 5-[1-hydroxy-2-(heterocyclic-amino)]alkyl-8-hydroxy-3,4-dihydrocarbostyril derivative of the formula (I) can be conducted by a conventional reduction using a reducing agent such as lithium aluminum hydride, sodium borohydride and the like, or a conventional catalytic reduction with hydrogen in the presence of a hydrogenation catalyst such as palladium black, palladium-on-carbon, Raney nickel, platinum black, platinum oxide and the like.

The above reducing agent can be used in an amount of from about 2 to about 10 moles, preferably 2 to 5 moles, per mole of the carbostyril compound of the formula (IIb) in a solvent while cooling under atmospheric pressure at a temperature of from about 0° to about 100° C., preferably 20° to 50° C. When sodium borohydride is used as the reducing agent, the solvent is preferably water or an alcohol such as methanol, ethanol and the like, and when lithium aluminum hydride is used as the reducing agent, the solvent is preferably a non-aqueous solvent such as anhydrous diethyl ether, ethyl acetate, tetrahydrofuran and the like.

The catalytic reduction can be carried out with hydrogen using the above hydrogenation catalyst in an amount of from about 0.05 to about 1 mole, preferably 0.1 to 0.5 mole, per mole of the carbostyril compound of the formula (IIb) in a solvent, for example, water or an alcohol such as methanol, ethanol or isopropanol under a hydrogen atmosphere at a pressure of from about atmospheric pressure to about 100 atmospheres, preferably atmospheric pressure to 50 atmospheres, at a temperature of from room temperature to about 150° C., preferably room temperature to 120° C., advantageously with agitating the reduction system. It is advantageous to carry out the above catalytic reduction at a temperature higher than about 50° C. at atmospheric pressure or at a temperature higher than room temperature under pressure.

Alternatively, the compound of the formula (I) of the present invention can also be prepared by catalytically reducing the corresponding 5-(α-heterocyclic-aminoalkanoyl)-8-hydroxy-carbostyril derivative having the formula (VII)

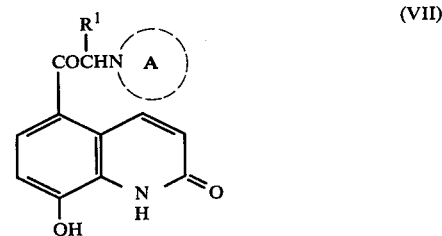

wherein $R^1$ and A are as defined above.

The 5-(α-heterocyclic-aminoalkanoyl)-8-hydroxycarbostyril derivative of the formula (VII) which can be used as a reactant in the above described reduction and a process for preparing the same are disclosed and claimed in co-pending application U.S. Patent Application Ser. No. 745,759, filed simultaneously herewith.

The catalytic reduction initially results in the production of a 5-(1-hydroxy-2-heterocyclic-aminoalkyl)-8-hydroxycarbostyril of the formula (VIII)

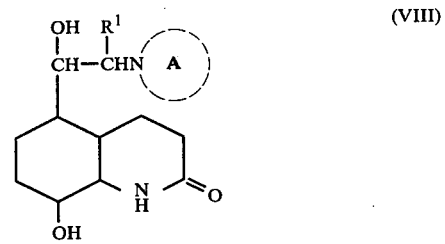

wherein $R^1$ and A are as defined above or the 5-(α-heterocyclic-aminoalkyanoyl)-8-hydroxy-3,4-dihydrocarbostyril having the formula (IIb) as described hereinbefore, which is then subjected to further reduction to form the compound of the formula (I).

The reduction of the 5-(α-heterocyclic-aminoalkanoyl)-8-hydroxycarbostyril derivative of the formula (VII) to the compound of the formula (I) can be carried out in a solvent such as water, methanol, ethanol, isopropanol, ethyl acetate and the like in the presence of a catalyst, e.g., palladium black, platinum oxide, palladium-on-carbon, platinum black, Raney nickel and the like at room temperature to about 150° C., preferably room temperature to 120° C. in a hydrogen atmosphere of about 1 to about 100, preferably 1 to 50, atmospheres.

The compound of the formula (I) can also be prepared by dealkylating the corresponding 5-[1-hydroxy-2-(heterocyclic-amino)]alkyl-8-alkoxy-3,4-dihydrocarbostyril derivative represented by the formula (IX)

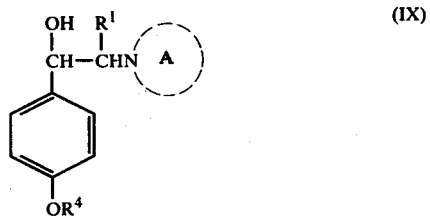 (IX)

wherein $R^1$, A and $R^4$ are as defined above with a hydrogen halide.

The 5-[1-hydroxy-2-(heterocyclic-amino)]alkyl-3,4-dihydrocarbostyril derivatives of the formula (IX) above and the process for preparing the same are disclosed in co-pending U.S. Patent Application Ser. No. 536,703, filed Dec. 26, 1974 now U.S. Pat. No. 4,022,784.

This dealkylation can be carried out under the same reaction conditions as used in this invention with respect to the dealkylation of the compound (IIa).

Both the compounds of the formula (IIa) and the compounds of the formula (I) as obtained above as basic substances and can form acid addition salts with various organic or inorganic acids. Particularly useful such salts are the pharmaceutically acceptable acid addition salts formed with inorganic acids such as hydrochloric acid, sulfuric acid, phosphoric acid, hydrobromic acid, etc., or organic acids such as oxalic acid, maleic acid, fumaric acid, malic acid, tartaric acid, citric acid, ascorbic acid, etc. These acid addition salts can easily be prepared by well-known procedures, for example, by adding an equimolar to an excess amount of the acid to a solution of the compound dissolved in an appropriate organic solvent such as methanol, ethanol, isopropanol, acetone and the like.

Both the free bases of the compounds (I) and the acid addition salts thereof exhibit a stimulating activity on β-adreno-receptor and, therefore, are very useful as pharmaceuticals for treating disorders such as bronchial asthma. As is apparent to one skilled in the art, the compounds of the present invention contain two asymmetrical centers and, therefore, can be present in four optically active forms. Particularly preferred compounds of the formula (I) are the following basic compounds and their hydrochlorides, sulfates, phosphates, maleates, fumarates and oxalates.

5-(1-Hydroxy-2-morpholino)propyl-8-hydroxy-3,4-dihydrocarbostyril 5-(1-Hydroxy-2-piperazino)butyl-8-hydroxy-3,4-dihydrocarbostyril 5-(1-Hydroxy-2-morpholino)butyl-8-hydroxy-3,4-dihydrocarbostyril 5-(1-Hydroxy-2-N-methylpiperazino)butyl-8-hydroxy-3,4-dihydrocarbostyril 5-(1-Hydroxy-2-Z-methylmorpholino)propyl-8-hydroxy-3,4-dihydrocarbostyril The present invention is further illustrated by reference to the following Examples, but these examples are given for the purposes of illustration and not to be construed as limiting the scope of the invention. Unless otherwise indicated, all parts, percents, ratios and the like are by weight.

EXAMPLE 1

17.1 g of α-bromopropionyl chloride (V), 27 g of anhydrous aluminum chloride and 8 ml of nitrobenzene were added to 8 g of 8-methoxy-3,4-dihydrocarbostyril (VI), and the mixture was heated at a temperature of 50° to 60° C. for one hour while stirring. The reaction mixture was then poured into 200 ml of ice-water, and the precipitate formed was filtered and washed with water. The precipitate was then recrystallized from ethanol to obtain 11.5 g of a material having a melting point of 154°-155° C. The product thus obtained was confirmed by NMR and IR spectral analyses and elemental analysis to be 5-(α-bromopropionyl)-8-methoxy-3,4-dihydrocarbostyril (IV).

EXAMPLE 2

26.4 g of α-bromobutyryl bromide (V), 17.5 g of anhydrous aluminum chloride and 5 ml of nitrobenzene were added to 5 g of 8-methoxy-3,4-dihydrocarbostyril (VI), and the mixture was heated at a temperature of 50° to 60° C. for one hour while stirring. The reaction mixture was then poured into 100 ml of ice-water, and the precipitate formed was filtered and washed with water. The precipitate was then recrystallized from ethano to obtain 5 g of a material having a melting point of 151°-152° C. The product thus obtained was confirmed by NMR and IR spectral analyses and elemental analysis to be 5-(α-bromobutyryl)-8-methoxy-3,4-dihydrocarbostyril (IV).

EXAMPLE 3

5 g of 5-(α-bromobutyl)-8-hydroxy-3,4-dihydrocarbostyril (IV) was suspended in 30 ml of benzene, and 4.2 ml of morpholine (III) was added to the suspension followed by allowing the mixture to react for 4 hours while heating under refluxing. The reaction mixture was filtered and the filtrate was washed with water followed by concentration under reduced pressure to remove any remaining water. The resulting residue was dissolved in 50 ml of isopropanol, and the solution was adjusted to a pH of 2-3 with concentrated hydrochloric acid. The viscous precipitate formed upon ice-cooling was separated and dissolved in acetone by heating. After allowing the solution to cool, the precipitate formed was dissolved in 30 ml of water and adjusted to a pH of 7.5-8 with sodium bicarbonate. The precipitate formed upon ice-cooling was filtered and dissolved in 10 ml of a 47% aqueous hydrobromic acid followed by concentration under reduced pressure. The residue thus obtained was washed with 10 ml of ethanol and recrystallized from ethanol to obtain 2.8 g of white amorphous 5-(α-morpholinobutyryl)-8-hydroxy-3,4-dihydrocarbostyril (IIb) hydrobromide monohydrate. The structure of the material thus obtained was confirmed by NMR and IR spectra and elemental analysis.

EXAMPLE 4

15 ml of a 47% aqueous hydrobromic acid was added to 2.0 g of 5-(1-hydroxy-2-morpholino)propyl-8-methoxy-3,4-dihydrocarbostyril (IX), and the mixture was heated under refluxing for a period of 10 hours. Thereafter, acetone was added to the reaction mixture to crystallize the product, and the resulting crystals were recrystallized from a mixture of ethanol and acetone to obtain 1.9 g of a material having a melting point of 183°–185° C. (with decomposition). The product thus obtained was confirmed by NMR and IR spectral analyses and elemental analysis to be 5-(1-hydroxy-2-morpholino)propyl-8-hydroxy-3,4-dihydrocarbostyril (I) hydrobromide.

EXAMPLE 5

1.0 g of 5-(2-morpholinobutyryl)-8-hydroxy-3,4-dihydrocarbostyril (IIb) hydrobromide was dissolved in 70 ml of water and 0.2 g of palladium-on-carbon and 0.3 g of palladium black were added to the solution followed by allowing the mixture to catalytically reduce under atmospheric pressure in a hydrogen atmosphere for 10 days at a temperature of 70° C. while shaking. After completion of the reduction, the reaction mixture was filtered to remove the catalysts by filtration, and the filtrate was concentrated to dryness under reduced pressure. The resulting residue was dissolved in acetone by heating followed by allowing the solution to cool. The precipitate formed upon cooling was recrystallized from ethanol to obtain 0.7 g of white amorphous 5-(2-morpholino-1-hydroxy)butyl-8-hydroxy-3,4-dihydrocarbostyril (I) hydrobromide ½ hydrate having a melting point of 183°–185° C. (with decomposition). The product thus obtained was confirmed by NMR and IR spectral analyses and elemental analysis.

EXAMPLE 6

10 g of the 5-(α-bromobutyryl)-8-hydroxy-3,4-dihydrocarbostyril (IV) was suspended in 50 ml of benzene, and 10 ml of piperazine (III) was added to the suspension followed by allowing the mixture to react while heating under refluxing and stirring for 6 hours. The reaction mixture was filtered to recover the reaction product which was then washed with benzene and then with 50 ml of isopropanol. The resulting insoluble material was dissolved in 150 ml of 2% aqueous hydrobromic acid. The solution was concentrated to dryness under reduced pressure and the resulting residue was recrystallized from ethanol to obtain 7.5 g of white amorphous 5-(α-piperazinobutyryl)-8-hydroxy-3,4-dihydrocarbostyril (IIb) dihydrobromide. The structure of the material thus obtained was confirmed by NMR and IR spectra and elemental analysis.

EXAMPLE 7

10 g of the 5-(α-bromobutyryl)-8-hydroxy-3,4-dihydrocarbostyril (IV) was suspended in 50 ml of benzene, and 10 ml of N-methylpiperazine (III) was added to the suspension followed by allowing the mixture to react while heating under refluxing and stirring for 6 hours. The reaction mixture was filtered to recover the reaction product which was then washed with benzene and then with 50 ml of isopropanol. The resulting insoluble material was dissolved in 150 ml of a 2% aqueous hydrobromic acid. The solution was concentrated to dryness under reduced pressure and the resulting residue was recrystallized from ethanol to obtain 8.5 g of white amorphous 5-(α-N-methylpiperazinobutyryl)-8-hydroxy-3,4-dihydrocarbostyril (IIb) dihydrobromide. The structure of the material thus obtained was confirmed by NMR and IR spectra and elemental analysis.

EXAMPLE 8

2.0 g of 5-(α-piperazinobutyryl)-8-hydroxy-3,4-dihydrocarbostyril (IIb) dihydrobromide was dissolved in 40 ml of water, and 0.5 g of palladium black as a catalyst was added to the solution. The mixture was stirred at a temperature of 70° to 75° C. under atmospheric pressure in the presence of hydrogen gas to absorb the hydrogen. After completion of the reduction, the catalyst was filtered and the filtrate was concentrated to dryness under reduced pressure. The water remaining in the resulting residue was then completely removed ethanol, and acetone was added to the residue to crystallize the product. Recrystallization from a mixture of water and acetone gave 1.1 g of a colorless amorphous material having a melting point of 228°–230° C. (dec.). The product thus obtained was confirmed by NMR and IR spectra and elemental analysis as 5-(1-hydroxy-2-piperazino)butyl-8-hydroxy-3,4-dihydrocarbostyril (I) dihydrobromide.

EXAMPLE 9

2.0 g of 5-(α-N-methylpiperazinobutyryl)-8-hydroxy-3,4-dihydrocarbostyril (IIb) dihydrobromide was dissolved in 40 ml of water, and 0.5 g of palladium black as a catalyst was added to the solution. The mixture was stirred at a temperature of 70° to 75° C. under atmospheric pressure in the presence of hydrogen gas to absorb the hydrogen. After completion of the reduction, the catalyst was filtered and the filtrate was concentrated to dryness under reduced pressure. The water remaining in the resulting residue was then completely removed ethanol, and acetone was added to the residue to crystallize the product. Recrystallization from a mixture of water and acetone gave 1.4 g of a colorless amorphous material having a melting point of 171°–173° C. (dec.). The product thus obtained was confirmed by NMR and IR spectra and elemental analysis as 5-(1-hydroxy-2-N-methylpiperazino)butyl-8-hydroxy-3,4-dihydrocarbostyril (I) dihydrobromide.

REFERENCE EXAMPLE

The stimulating activity of the compounds of this invention on β-adreno-receptor was determined using guinea-pig trachea as follows:

The trachea was excised from male Hartley strain guinea pigs weighing from 450–600 g. Spiral fashion of trachea was prepared as described by Constantine (1965), and suspended in a 30 ml tissue bath containing Tyrode solution maintained at 36° C. and aerated with 95% $O_2$ — 5% $CO_2$. Resting tension was maintained at 2 g during experiments. Mortality of tracheal muscle was monitered by isometric recordings using force transducers (San-ei Sokki, Type 45072).

Phentolamine, $10^{-5}$ M was added to bath fluid 30 min before contraction with acetylcholine, $10^{-5}$ g/ml in order to block α-adrenergic receptors, and the relaxation produced by test compounds shown in Table 1 was studied after contraction with acetylcholine. The test compound was added to bath fluid using a cumulative method of drug administration by Van Rossum (1963). Responses were expressed as a percentage of the maximum possible response of each tissue obtained by the addition of the doses of isoproterenol which induced the maximal relaxation of tracheal muscle. $ED_{50}$ values of test compounds were determined from each dose-response curve and compared with that of isoproterenol. The results obtained are shown in Table 1.

Table 1

| Sample | Bronchial Resistance | |
|---|---|---|
| | $ED_{50}$ | $\dfrac{ED_{50} \text{ of Isoproterenol}}{ED_{50} \text{ of Sample}} \times 100$ |
| 5-(1-Hydroxy-2-piperazino)butyl-8-hydroxy-3,4-dihydrocarbostyril Hydrobromide | $3.0 \times 10^{-8}$ | 278 |
| 5-(1-Hydroxy-2-N-methylpiperazino)butyl-8-hydroxy-3,4-dihydrocarbostyril Hydrobromide | $4.7 \times 10^{-8}$ | 178 |
| 5-(1-Hydroxy-2-morpholino)butyl-8-hydroxy-3,4-dihydrocarbostyril Hydrochloride | $2.5 \times 10^{-8}$ | 334 |
| Isoproterenol | $8.35 \times 10^{-8}$ | 100 |

From the results shown in Table 2 it is apparent that the compounds of this invention have $ED_{50}$ values about ⅓ times as small as that of isoproterenol, which means the former compounds are superior over the latter compounds as a β-adrenergic stimulating agent.

In order to investigate side effects of the above-described test compounds, $ED_{30}$, which corresponds to effects on atria, of the respective compounds were determined using guinea pig atria as follows:

Right atria were excised from male Hartley strain guinea pigs weighing 450 to 600 g, and suspended in a 30 ml tissue bath containing Lock solution maintained at 36° C. and aerated with 95% $O_2$ — 5% $CO_2$. Spontaneous contraction rate was obtained from isometric recordings using force transducers (San-ei Sokki, Type 45072). The resting tension was maintained at 0.5 g for each atria. The test compounds as shown in Table 1 were added to bath fluid at a single dose for each response.

Effective doses ($ED_{30}$ values) of the test compound which induced 30 beats/min increase in contractile rate were determined and compared with that of isoproterenol.

The results obtained are shown in Table 2.

Table 2

| Sample | Side Effect | |
|---|---|---|
| | $ED_{30}$ | $\dfrac{ED_{30} \text{ of Isoproterenol}}{ED_{30} \text{ of Sample}} \times 1,000$ |
| 5-(1-Hydroxy-2-piperazino)butyl-8-hydroxy-3,4-dihydrocarbostyril Hydrobromide | $1.9 \times 10^{-9}$ | 105 |
| 5-(1-Hydroxy-2-N-methylpiperazino)butyl-8-hydroxy-3,4-dihydrocarbostyril Hydrobromide | $2.0 \times 10^{-9}$ | 100 |
| 5-(1-Hydroxy-2-morpholino)butyl-8-hydroxy-3,4-dihydrocarbostyril Hydrochloride | $1.8 \times 10^{-9}$ | 111 |
| Isoproterenol | $2.0 \times 10^{-10}$ | 1000 |

From the results shown in Table 2 it is clear that the side effect of the compound of this invention is much less, than that of Isoproterenol.

Further, the acute toxicity was determined with respect to the test compounds shown in Table 3 below using 5 to 6 groups each containing 10 male rats (dd strain; body weight, 18 to 22 g) which had been fasted for 12 hours prior to the test. Isoproterenol was used as a control. The $LD_{50}$ (50% lethal dose) results are as follows.

Table 3

| Compound | $LD_{50}$ (mg/kg) i.v. |
|---|---|
| 5-(1-Hydroxy-2-piperazino)-butyl-8-hydroxy-3,4-dihydro-carbostyril Hydrobromide | 105 (93–130) |
| 5-(1-Hydroxy-2-piperazino)-butyl-8-hydroxy-3,4-dihydrocarbostyril Hydrobromide | 95 (87–110) |
| 5-(1-Hydroxy-2-morpholino)-butyl-8-hydroxy-3,4-dihydro-carbostyril Hydrochlride | 95 (88–117) |
| Isoproterenol | 94 (78–121) |

From the results shown in Table 3, it can be seen that $LD_{50}$ values of the compounds of the present invention are substantially the same as or slightly improved as compared with those of isoproterenol.

In view of the results shown in Table 1 to 3, it is concluded that the compounds of this invention are highly improved in their side effects, while they have a good β-adrenergic stimulating activity, with the toxicity remaining substantially the same as or being slightly improved as compared with those exhibited by the conventional compound.

The compounds of the present invention can be administered at a dosage level of from 100 to 50 mg/kg/day by oral, intravenous, intramuscular, intrarectal or inhalational administration in a conventional pharmaceutical dosage from such as a tablet, powder, granule, capsule, syrup, solution, suspension, inhalant (aerosol spray), suppository and the like, preferably, in combination with pharmaceutically acceptable carriers or diluents which are well known in the art.

Pharmaceutical compositions generally comprise at least one compound of the present invention and pharmaceutical carriers or diluents which are commonly employed in conventional pharmaceutical compositions. The compositions may contain other active components which do not adversely affect the activities of the compounds of this invention.

Suitable pharmaceutical carriers or diluents include solid carriers such as corn starch, calcium sulfate dihydrate, magnesium stearate, lactose, Aerosil (tradename of Nihon Aerosil Co., Ltd. Japan) and the like which are suitable for use in oral, suppository, injectable and inhalant formulations. The oral dosage forms can be formulated in accordance with well known procedures and conveniently formulated into tablets which can be optionally provided with a sugar coating. A soluble tablet which is suitable for sublingual administration, i.e., troche or lozenge, can also be prepared.

The injectable composition can be prepared using phydiologically acceptable carriers or diluents in the form of solution, suspension or dry preparation which is reconstituted instantaneously with a vehicle for injection just before administration.

The compounds of the present invention are advantageously administered in the form of an aerosol spray formulation by inhalation.

Typical examples of suitable formulations are given below, but it is to be noted that other dosage forms can also be prepared using other compounds of this invention according to the well-established pharmaceutical techniques.

FORMULATION 1

Tablets each containing the following components were prepared from the following components:

| Component | Amount |
|---|---|
| 5-(1-Hydroxy-2-piperazino)butyl-8-hydroxy-3,4-dihydrocarbostyril | 1 mg |
| Corn Starch | 70 mg |
| Magnesium stearate | 9 mg |
| Lactose | 20 mg |
| Total | 100 mg |

FORMULATION 2

Tablets each containing the following components were prepared from the following components:

| Component | Amount |
|---|---|
| 5-(1-Hydroxy-2-morpholino)butyl-8-hydroxy 3,4-dihydrocarbostyril | 1 mg |
| Corn Starch | 70 mg |
| Magnesium stearate | 9 mg |
| Lactose | 20 mg |
| Total | 100 mg |

FORMULATION 3

Aerosol spray for inhalation containing the following components per each dose was prepared and filled in the aerosol dispenser:

| Components | Amount |
|---|---|
| 5-(1-Hydroxy-2-N-methylpiperazino)butyl-8-hydroxy-3,4-dihydrocarbostyril | 50 mcg |
| Oleic Acid | 10 mcg |
| Dichlorodifluoromethane | 57 mcg |
| Trichlorofluoromethane | 25 mcg |

FORMULATION 4

Aerosol spray for inhalation containing the following components per each dose was prepared and filled in the aerosol dispenser:

| Components | Amount |
|---|---|
| 5-(1-Hydroxy-2-morpholino)propyl-8-hydroxy-3,4-dihydrocarbostyril | 50 mcg |
| Oleic Acid | 10 mcg |
| Dichlorodifluoromethane | 57 mcg |
| Trichlorofluoromethane | 25 mcg |

While the present invention has been described in detail and with reference to specific embodiments thereof, it will be apparent to one skilled in the art that various changes and modifications can be made therein without departing from the spirit and scope thereof.

What is claimed is:

1. A 5-[1-hydroxy-2-(heterocyclic-amino)]alkyl-8-hydroxy-3,4dihydrocarbostyril derivative having the formula

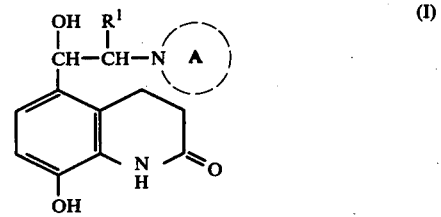

wherein $R^1$ represents an alkyl group having 1 to 4 carbon atoms, and A, when taken together with the nitrogen atom to which it is attached, forma a morpholino or piperazino ring which is unsubstituted or substituted by an alkyl group of 1 to 4 carbon atoms, and the pharmaceutically acceptable acid addition salts thereof.

2. 5-(1-Hydroxy-2-morpholino)propyl-8-hydroxy-3,4-dihydrocarbostyril according to claim 1.

3. 5-(1-Hydroxy-2-morpholino)butyl-8-hydroxy-3,4-dihydrocarbostyril according to claim 1.

* * * * *

UNITED STATES PATENT AND TRADEMARK OFFICE
CERTIFICATE OF CORRECTION

PATENT NO. : 4,145,542

DATED : March 20, 1979

INVENTOR(S) : Kazuyuki NAKAGAWA et al

It is certified that error appears in the above-identified patent and that said Letters Patent are hereby corrected as shown below:

IN THE HEADING:

Foreign Application Priority Data:

Insert -- Nov. 11, 1974  Japan ............. 49-130721 --

-- Nov. 11, 1974  Japan ............. 49-130722 --

-- Nov. 11, 1974  Japan ............. 49-130723 --

-- Nov. 11, 1974  Japan ............. 49-130724 --

-- Nov. 11, 1974  Japan ............. 49-130725 --

-- Nov. 11, 1974  Japan ............. 49-130728 --

-- Dec.  4, 1974  Japan ............. 49-140339 --

-- Dec.  4, 1974  Japan ............. 49-140340 --

Signed and Sealed this

Twenty-ninth Day of May 1979

[SEAL]

Attest:

RUTH C. MASON
*Attesting Officer*

DONALD W. BANNER
*Commissioner of Patents and Trademarks*